(12) United States Patent
Liebminger et al.

(10) Patent No.: US 10,881,107 B2
(45) Date of Patent: Jan. 5, 2021

(54) ANTIMICROBIAL COMPOSITIONS CONTAINING ALKYLPYRAZINES AND THEIR USES

(71) Applicant: ROOMBIOTIC GMBH, Graz (AT)

(72) Inventors: Stefan Liebminger, Graz (AT); Gabriele Berg, Graz (AT); Laura Lange, Raaba (AT)

(73) Assignee: Roombiotic GmbH, Graz (AT)

( * ) Notice: Subject to any disclaimer, the term of this patent is extended or adjusted under 35 U.S.C. 154(b) by 404 days.

(21) Appl. No.: 15/752,204

(22) PCT Filed: Aug. 12, 2016

(86) PCT No.: PCT/EP2016/069219
§ 371 (c)(1),
(2) Date: Feb. 12, 2018

(87) PCT Pub. No.: WO2017/025621
PCT Pub. Date: Feb. 16, 2017

(65) Prior Publication Data
US 2020/0205410 A1  Jul. 2, 2020

(30) Foreign Application Priority Data
Aug. 13, 2015 (GB) .................. 1514384.5

(51) Int. Cl.
| | |
|---|---|
| A01N 43/60 | (2006.01) |
| A01N 25/10 | (2006.01) |
| A22B 5/00 | (2006.01) |
| A23B 4/20 | (2006.01) |
| A23B 9/26 | (2006.01) |
| A23L 3/3544 | (2006.01) |
| C02F 1/68 | (2006.01) |

(52) U.S. Cl.
CPC ............ *A01N 43/60* (2013.01); *A01N 25/10* (2013.01); *A22B 5/0082* (2013.01); *A23B 4/20* (2013.01); *A23B 9/26* (2013.01); *A23L 3/3544* (2013.01); *C02F 1/68* (2013.01)

(58) Field of Classification Search
None
See application file for complete search history.

(56) References Cited

U.S. PATENT DOCUMENTS

| 3,544,682 A | 12/1970 | Taylor et al. |
| 4,126,618 A | 11/1978 | Winter et al. |
| 2004/0234479 A1 | 11/2004 | Schleifenbaum et al. |

FOREIGN PATENT DOCUMENTS

| DE | 1913726 | 10/1969 |
| GB | 1 268 448 | 3/1972 |
| JP | 2003-95950 A | 4/2003 |
| JP | 2014-224103 A | 12/2014 |
| JP | 2015-113295 A | 6/2015 |
| WO | WO 99/37152 | 7/1999 |
| WO | WO 2012/085255 A2 | 6/2012 |

OTHER PUBLICATIONS

Schulz etal., Marine Drugs (2010), 8, pp. 2976-2987.*
International Search Report and Written Opinion of the International Searching Authority of corresponding PCT/EP2016/069219, dated Sep. 28, 2016, 14 pages.
British Search Report for GB 1514384.5, dated Feb. 25, 2016, 6 pages.
Beck, et al. "Novel pyrazine metabolites found in polymyxin biosynthesis by Paenibacillus polymyxa," FEMS Microbiology Letters, vol. 220, No. 1, 2003, pp. 67-73.

* cited by examiner

*Primary Examiner* — Brian J Davis
(74) *Attorney, Agent, or Firm* — Lewis Roca Rothgerber Christie LLP

(57) ABSTRACT

Embodiments of the invention relates to an antimicrobial composition comprising an alkyl pyrazine compound or mixture of compounds selected from the group consisting of 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents. Further embodiments of the invention relate to uses of alkyl pyrazine compounds, in particular for controlling microbial growth.

4 Claims, 1 Drawing Sheet

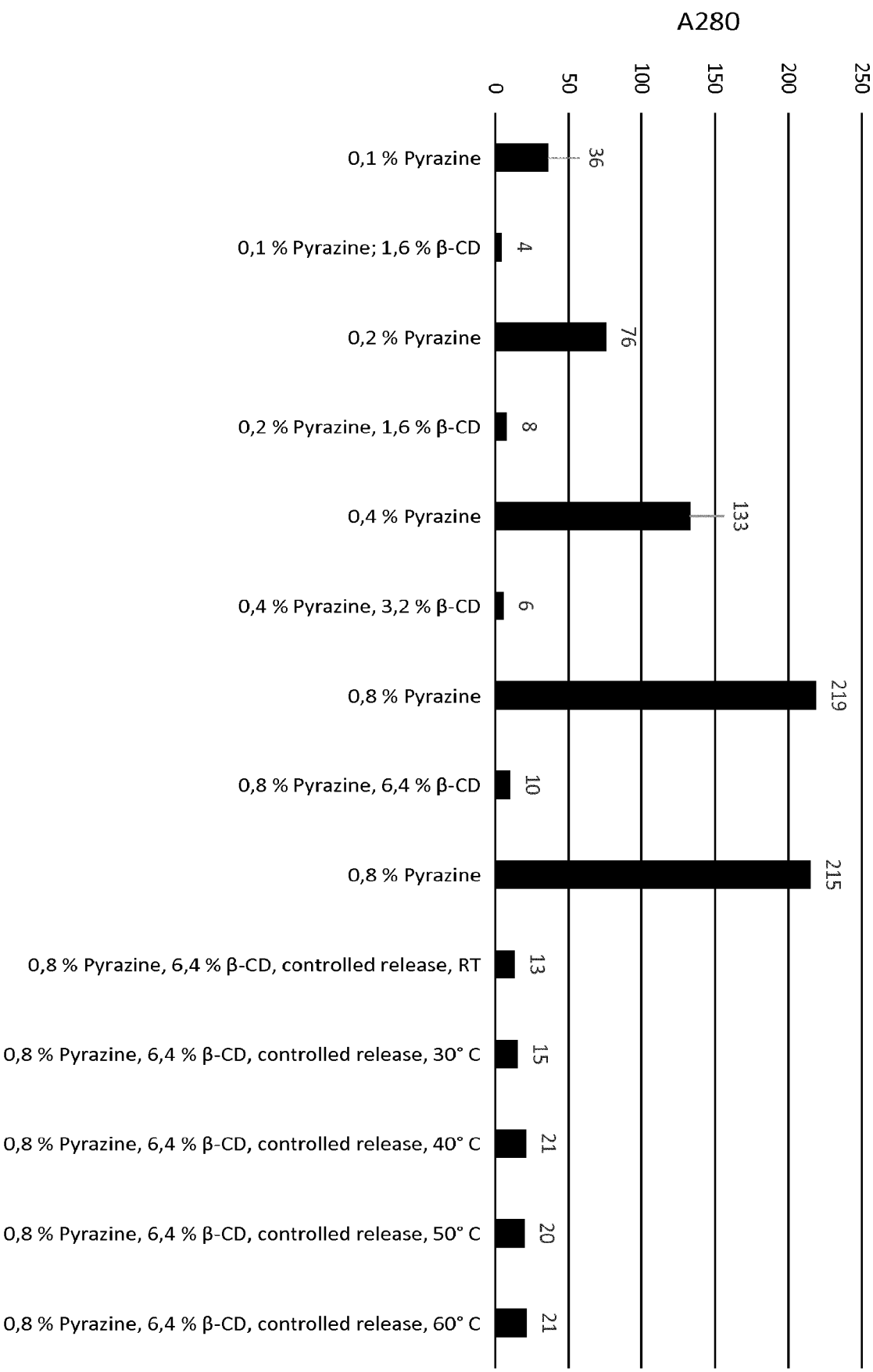

ANTIMICROBIAL COMPOSITIONS CONTAINING ALKYLPYRAZINES AND THEIR USES

CROSS-REFERENCE TO RELATED APPLICATION(S)

This application is the U.S. national phase of International Application No. PCT/EP2016/069219 filed 12 Aug. 2016 which designated the U.S. and claims priority to British Patent Application No. 1514384.5 filed 13 Aug. 2015, the entire contents of each of which are hereby incorporated herein by reference.

FIELD OF THE INVENTION

Embodiments of the invention relate to antimicrobial compositions (or agents) and to uses of alkyl pyrazine compounds, in particular for controlling microbial growth.

BACKGROUND

The removal of microbial contaminants from environments or materials is of utmost importance in many applications. The presence of such microbial contaminants may have detrimental effects, for example if these contaminants are pathogenic, and thus may cause medical conditions in organisms being in contact with them. Additionally or alternatively, microbial contaminants may also interfere with the production process of various industrial goods, such as food or seeds. In large quantities, microbial contaminants may even form undesired biofilms.

In an attempt to cope with microbial contaminants in clean room environments and clinical settings, WO 2012/085255 A2 proposes the use of volatile organic compounds produced by plant-associated microorganism.

However, there still remains a need for antimicrobial agents and compositions that are highly effective and can be versatilely used, in particular also in industrial environments, such as in the production of food, the purification of water, the industrial processing of meat and stock farming, just to name a few.

Accordingly, there may be a need to provide such antimicrobial agents and compositions as well as uses thereof.

SUMMARY OF THE INVENTION

The present inventors have made diligent studies for solving these objects and have found that specific alkyl pyrazine compounds not only have a high antimicrobial activity but are also volatile so that they can be versatilely employed. The present inventors have found that pyrazine compounds having (bearing) at least one isopropyl and/or isobutyl substituent (moiety, residue) are particular promising antimicrobial agents. Among these, 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents have proven to be of particular suitability.

Accordingly, an exemplary embodiment of the invention relates to an antimicrobial composition (or antimicrobial agent) comprising (or consisting of) an alkyl pyrazine compound or mixture of compounds selected from the group consisting of 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents.

A further exemplary embodiment of the invention relates to the use of an alkyl pyrazine compound or mixture of compounds selected from the group consisting of 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents as an antimicrobial agent (such as for controlling microbial growth).

A still further exemplary embodiment of the invention relates to the use of an alkyl pyrazine compound having at least one isopropyl and/or isobutyl substituent for controlling microbial growth in and/or on any one of the group consisting of food, seeds, water and biofilms.

A still further exemplary embodiment of the invention relates to the use of an alkyl pyrazine compound having at least one isopropyl and/or isobutyl substituent as an antimicrobial agent in any one of the group consisting of the industrial production and/or storage of foods, the storage of seed, the purification of water, stock farming and industrial meat processing.

Other objects and many of the attendant advantages of embodiments of the invention will be readily appreciated and become better understood by reference to the following detailed description of embodiments.

BRIEF DESCRIPTION OF THE DRAWINGS

The FIGURE shows experimental results about the influence of the encapsulation of an alkyl pyrazine compound in a cyclodextrin on the release properties of the alkyl pyrazine compound.

DETAILED DESCRIPTION OF THE INVENTION

Hereinafter, details of embodiments of the invention and other features and advantages thereof will be described. However, the invention is not limited to the following specific descriptions, but they are rather for illustrative purposes only.

It should be noted that features described in connection with one exemplary embodiment or exemplary aspect may be combined with any other exemplary embodiment or exemplary aspect, in particular features described with any exemplary embodiment of an antimicrobial composition may be combined with any exemplary embodiment of the uses of alkyl pyrazine compounds and vice versa, unless specifically stated otherwise. In addition, any exemplary embodiment or feature of the uses of alkyl pyrazine compounds of any one of the second, third and fourth aspect may be combined among each other.

Where an indefinite or definite article is used when referring to a singular term, such as "a", "an" or "the", a plural of that term is also included and vice versa, unless specifically stated otherwise, whereas the word "one" or the number "1", as used herein, typically means "just one" or "exactly one".

The expression "comprising", as used herein, includes not only the meaning of "comprising", "including" or "containing", but also encompasses "consisting essentially of" and "consisting of".

In a first aspect, an exemplary embodiment of the invention relates an antimicrobial composition (or antimicrobial agent) comprising (or consisting of) an alkyl pyrazine compound or mixture of (alkyl pyrazine) compounds selected from the group consisting of 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents.

In other words, the alkyl pyrazine compound or mixture of compounds comprised in the antimicrobial composition is at least one of the group consisting of 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents.

In an embodiment, the antimicrobial composition may consist of the at least one alkyl pyrazine compound or mixture of compounds. Thus, the antimicrobial composition may also be referred to as antimicrobial agent or mixture of antimicrobial agents.

The term "antimicrobial agent" or "antimicrobial composition", as used herein, may in particular mean a compound or mixture of compounds having an inhibitory (or antagonistic) effect on the growth of microorganisms, that is, compounds that are capable of at least reducing the growth rate (e.g. bacteriostatic agents with respect to controlling the growth of bacteria) as well as compounds that cause toxic effects (e.g. bactericide agents killing bacteria).

The term "controlling microbial growth", as used herein, denotes any activity for completely inhibiting or at least reducing the growth of microorganisms such as bacteria, archaea, yeasts, fungi, viruses, and the like, in a given environment. In particular, the term relates to biologically controlling microbial growth of said microorganisms, that is, by employing biological means as "growth inhibitors or growth reducing agents". The term "inhibiting", as used herein, is to be understood as not only to include the prevention of further growth of but also to killing of any given microorganisms. The term "reducing", as used herein, denotes any decrease in an microorganism's growth (or growth rate), for example, a decrease of at least 5%, 10%, 15%, 20%, 25%, 30%, 40%, 50%, 60%, 70%, 80%, 85%, 90% or 95% as compared to control conditions (i.e. in the absence of antimicrobial agents according to embodiments of the invention).

The term "microorganisms", as used herein, denotes any microscopic organism (i.e. organisms too small to be seen by the naked human eye) including both prokaryotic and eukaryotic organism as well as both single cell-organisms and multi-cellular organisms. Examples of microorganisms include inter alia bacteria, archaea (archaebacteria), fungi, yeasts, viruses, and protists (e.g., algae, dinoflagellates, amoebae, *Plasmodium* spec., and *Euglena* spec.).

An alkyl pyrazine compound comprises a pyrazine ring (or 1,4-diazine ring), i.e. an aromatic 6-membered ring wherein two carbon atoms in para-position to each other are replaced by nitrogen atoms, having (bearing) at least one alkyl substituent (moiety, residue), in particular 1, 2, 3 or 4 alkyl substituents. The alkyl pyrazine compounds according to embodiments of the invention in particular comprise at least one isopropyl (1-methylethyl) and/or isobutyl (2-methylpropyl) substituent. Preferably, the alkyl pyrazine compounds according to embodiments of the invention comprise one or two substituents selected from isopropyl and/or isobutyl. In addition to the at least one isopropyl and/or isobutyl substituent, the alkyl pyrazine compound may comprise further substituents, for instance further alkyl substituents, such as methyl, ethyl or propyl, or alkoxy substituents. Without wishing to be bound to any theory, the present inventors assume that the presence of at least one isopropyl and/or isobutyl substituent at the pyrazine ring is important for imparting the pyrazine compound with both antimicrobial activity and volatility.

The alkyl pyrazine compound may in particular be selected from the group consisting of 2-isobutyl-3-methylpyrazine, 2-isobutyl-3-methoxypyrazine, 2-isopropylpyrazine, 2-isobutylpyrazine, as well as combinations of any two or more of the foregoing. These alkyl pyrazine compounds have proven to be of particular suitability in terms of antimicrobial activity and volatility.

The alkyl pyrazine compound may in particular also be a mixture of methylpyrazines having one, two and three isopropyl or isobutyl substituents, such as a mixture of at least one methylpyrazine having one isopropyl substituent, at least one methylpyrazine having two isopropyl substituents and at least one methylpyrazine having three isopropyl substituents, a mixture of at least one methylpyrazine having one isobutyl substituent, at least one methylpyrazine having two isobutyl substituents and at least one methylpyrazine having three isobutyl substituents or a mixture of at least one methylpyrazine having one isopropyl or isobutyl substituent, at least one methylpyrazine having two isopropyl and/or isobutyl substituents and at least one methylpyrazine having three isopropyl and/or isobutyl substituents.

A methylpyrazine having one isopropyl substituent denotes a compound with a pyrazine ring bearing as substituents a methyl group and one isopropyl group. Similarly, a methylpyrazine having two isopropyl substituents denotes a compound with a pyrazine ring bearing as substituents a methyl group and two isopropyl groups. Likewise, a methylpyrazine having three isopropyl substituents denotes a compound with a pyrazine ring bearing as substituents a methyl group and three isopropyl groups. It should be noted that the methyl and isopropyl substituents may be at any one of the 2-, 3-, 5- and 6-position of the pyrazine rings. Likewise, a methylpyrazine having one isobutyl substituent denotes a compound with a pyrazine ring bearing as substituents a methyl group and one isobutyl group, a methylpyrazine having two isobutyl substituents denotes a compound with a pyrazine ring bearing as substituents a methyl group and two isobutyl groups, a methylpyrazine having three isobutyl substituents denotes a compound with a pyrazine ring bearing as substituents a methyl group and three isobutyl groups, and the methyl and isobutyl substituents may be at any one of the 2-, 3-, 5- and 6-position of the pyrazine rings.

The mixture of methylpyrazines having one, two and three isopropyl substituents may for example include
- 5 to 90 wt.-% of methylpyrazine(s) having one isopropyl substituent, such as 10 to 80 wt.-%, in particular 20 to 70 wt.-%,
- 10 to 95 wt.-% of methylpyrazine(s) having two isopropyl substituents, such as 15 to 90 wt.-%, in particular 20 to 80 wt.-%, and
- 1 to 20 wt.-% of methylpyrazine(s) having three isopropyl substituents, such as 2 to 15 wt.-%, in particular 5 to 10 wt.-%.

The alkyl pyrazine compounds may be synthetically prepared by well-known synthetic methods, such as the reaction of diamines with diols in a vapor phase reaction in the presence of a catalytic system. Thus, the alkyl pyrazine compounds may represent synthetic compounds. Some of the alkyl pyrazine compounds may also exist in nature, such as in plants or microorganism, from which they can be isolated and optionally further chemically modified. Thus, the alkyl pyrazine compounds may also represent natural or semi-synthetic compounds. Alkyl pyrazine compounds may also be formed by the Maillard reaction (i.e. the chemical reaction between amino acids and reducing sugars that typically occurs in food upon cooking and frying).

In an embodiment, the antimicrobial composition may further comprise an additional (i.e. in addition to the alkyl pyrazine compound or mixture of compounds selected from the group consisting of 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents) alkyl pyrazine compound having at least one isopropyl and/or isobutyl substituent. The additional alkyl pyrazine compound having at least one isopropyl and/or isobutyl substituent may comprise one, two, three or four substituents selected from isopropyl and/or isobutyl, preferably one or two thereof. In addition to the at least one isopropyl and/or isobutyl substituent, the additional alkyl pyrazine compound may comprise further substituents, for instance further alkyl substituents, such as methyl, ethyl or propyl, or alkoxy substituents. Such combinations of antimicrobial alkyl pyrazine compounds may provide for a synergistic antimicrobial effect and/or may be suitable for controlling the microbial growth of a particular wide range of microorganisms. Of course, the antimicrobial composition may also comprise further antimicrobial agents other than alkyl pyrazine compounds having at least one isopropyl and/or isobutyl substituent.

In an embodiment, the antimicrobial composition may be present in solid, liquid or gaseous form.

For example, the antimicrobial composition may be present in solid form (e.g. as a powder). In particular, the alkyl pyrazine compounds may be mixed with solid excipients or fillers, such as solid organic or inorganic compounds.

Alternatively, the antimicrobial composition may be present in liquid form. The alkyl pyrazine compounds are typically liquid at room temperature (e.g. at 20° C.) and at normal pressure (e.g. at 1013 mbar). Thus, when applied in pure form (for example if the antimicrobial composition consists of the alkyl pyrazine compounds), the antimicrobial composition is typically also liquid at room temperature. However, the antimicrobial composition may also be a solution or a dispersion, such as a suspension or an emulsion.

As a further alternative, the antimicrobial composition may be present in gaseous form. As previously mentioned, the alkyl pyrazine compounds may be volatile compounds, i.e. compounds having a high vapor pressure at room temperature. In addition, such alkyl pyrazine compounds in the gas phase may be further mixed with other gases.

In a particular embodiment, the antimicrobial composition may be present in the form of an aerosol, in particular when being sprayed.

In an embodiment, the antimicrobial composition may further comprise a solvent. The solvent is not particularly limited, as long as it is capable to at least partly dissolve the alkyl pyrazine compounds. Suitable examples thereof include water, ethanol, an oily liquid or a mixture thereof.

In an embodiment, the antimicrobial composition may further comprise a carrier material, wherein the alkyl pyrazine compound (or mixture of compounds) is immobilized on and/or in the carrier material. A "carrier" as used herein may in particular denote a (solid) material that is inert and does not possess any substantial antimicrobial activity, but is capable of "carrying" or immobilizing the alkyl pyrazine compounds. As a result of the immobilization on and/or in the carrier material, the stability (or resistance to environmental influences) of the alkyl pyrazine compounds may be increased. As a further result, it might be possible to achieve a controlled release of the alkyl pyrazine compounds from the carrier, for example by means of thermal processes or by variations of the (air) humidity.

In an embodiment, the carrier material may comprise a cyclodextrin. Cyclodextrins are compounds made up of sugar molecules bound together to form a ring. Suitable examples include α-cyclodextrins (6-membered sugar rings), β-cyclodextrins (7-membered sugar rings) and γ-cyclodextrins (8-membered sugar rings), in particular α-cyclodextrins and β-cyclodextrins, and more particularly β-cyclodextrins. The cyclodextrin molecules may also be functionalized, for instance by polar groups, such as carboxyl moieties, which may be in particular suitable to improve the solubility thereof in aqueous liquids. Cyclodextrins are in particular suitable carrier materials for the alkyl pyrazine compounds in that they enable the formation of host-guest complexes, such as by including the alkyl pyrazine compounds within the toroid structure of the dextrin molecules, thereby providing efficient protection for the alkyl pyrazine compounds against environmental influences as well as enabling controlled release in a tailored manner. The weight ratio of the cyclodextrin to the alkyl pyrazine compounds may be for instance in the range of from 3:1 to 25:1, in particular from 5:1 to 20:1.

In a second aspect, an exemplary embodiment of the invention relates to the use of an alkyl pyrazine compound or mixture of compounds selected from the group consisting of 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents as an antimicrobial agent (such as for controlling microbial growth).

In an embodiment, the alkyl pyrazine compound or mixture of compounds may be used for controlling microbial growth in and/or on any one of the group consisting of food, seeds, water and biofilms.

In an embodiment, the antimicrobial agent may be used in any one of the group consisting of the industrial production and/or storage of foods, the storage of seed, the purification of water, stock farming and industrial meat processing.

In a third aspect, an exemplary embodiment of the invention relates to the use of an alkyl pyrazine compound having at least one isopropyl and/or isobutyl substituent for controlling microbial growth in and/or on any one of the group consisting of food, seeds, water and biofilms.

In a forth aspect, an exemplary embodiment of the invention relates to the use of an alkyl pyrazine compound having at least one isopropyl and/or isobutyl substituent as an antimicrobial agent in any one of the group consisting of the industrial production and/or storage of foods, the storage of seed, the purification of water, stock farming and industrial meat processing.

In an embodiment of the second, the third and the forth aspect, a mixture of at least two alkyl pyrazine compounds (for example, two, three, four, five or more alkyl pyrazine compounds) may be used.

In an embodiment of the third and the forth aspect, the alkyl pyrazine compound having at least one isopropyl and/or isobutyl substituent may be free of a polar and/or a charged substituent, such as a hydroxy substituent and/or an amino (amine) substituent, i.e. does not comprise a polar and/or a charged substituent, such as a hydroxy substituent and/or an amino (amine) substituent. Hereby, a particular advantageous volatility of the alkyl pyrazine compound may be achieved enabling a particular versatility of employment.

In an embodiment, the alkyl pyrazine compounds may be used for the treatment of surfaces, such as those made of metal, glass, plastics or textile tissues. The alkyl pyrazine compounds may be applied for instance in pure form or in the form of a solution to the surface to be treated, for example by spraying or wiping. After a predetermined (incubation) time, they can be removed again either actively (for example by wiping) or passively (for example by evaporation in view of their volatility).

In an embodiment, the alkyl pyrazine compounds may be used for the treatment (such as for controlling microbial growth in and/or on) of food. The alkyl pyrazine compounds may be applied in and on the food, for example as an ingredient of the food (e.g. as flavoring agent or as processing additive) or may be applied to the surface of the food (for example by spraying or dipping). The alkyl pyrazine compounds may be used in the (industrial) production and/or the storage of the food. Suitable examples for the food to be treated include bakery products, meat, fish, fruits and vegetables.

In an embodiment, the alkyl pyrazine compounds may be used for the treatment (such as for controlling microbial growth in and/or on) of seeds, for example during the storage thereof.

In an embodiment, the alkyl pyrazine compounds may be used for the treatment, such as the purification in terms of microbial load, of water, in particular of drinking water (tap water), waste water (sewage) or process water. The alkyl pyrazine compounds may be added to the water to be treated wherein they may exhibit a particularly high antimicrobial activity. Subsequently, the alkyl pyrazine compounds can be removed, for example by thermal treatment or by immobilization.

In an embodiment, the alkyl pyrazine compounds may be used for the treatment (in particular the degradation or removal) of biofilms. The term "biofilm", as used herein, may in particular denote a group of microorganisms in which cells stick to each other on a surface. These adherent cells may be embedded within a self-produced matrix of extracellular polymeric substance, which may also be referred to as a slime.

In an embodiment, the alkyl pyrazine compounds may be used in stock farming. In particular, animal feed may be treated with the alkyl pyrazine compounds to thereby control the growth of microorganisms.

In an embodiment, the alkyl pyrazine compounds may be used in industrial meat processing. The alkyl pyrazine compounds may be applied to the animal bodies (carcass), the equipment used in slaughterhouses, food packaging, and the like.

In an embodiment, the antimicrobial agent (the alkyl pyrazine compound) is effective against at least one microorganism or the microbial growth of at least one microorganism is controlled, wherein the at least one microorganism is selected from the group consisting of gram-negative bacteria, gram-positive bacteria, yeast-like fungi and mould-like fungi.

In particular, the at least one microorganism may be selected from the group consisting of *Escherichia coil, Stenotrophomonas maltophllia, Pseudomonas aeruginosa, Salmonella typhimurium, Bacillus subtilis, Listeria monocytogenes, Nocardia* sp., *Staphylococcus aureus, Staphylococcus epidermis, Candida albicans* and *Penicillium* sp. In a particular advantageous embodiment, the antimicrobial agent (the alkyl pyrazine compound) is effective against at least two, three, four, five and in particular any one of these microorganisms.

Embodiments of the invention are further described by the following examples, which are solely for the purpose of illustrating specific embodiments, and are not construed as limiting the scope of the invention in any way.

EXAMPLES

Example 1

Several alkyl pyrazine compounds or mixtures thereof have been tested for their antimicrobial activity. The results of these tests are summarized in Table 1.

TABLE 1

| Compound | Antimicrobial activity | Degree of antimicrobial activity | Natural origin |
| --- | --- | --- | --- |
| 2,3-Dimethylpyrazine (*) | Yes | Weak | Yes |
| 2,5-Dimethylpyrazine (*) | Yes | Weak | Yes |
| 2,3,5-Trimethylpyrazine (*) | No | — | Yes |
| 2-Isobutyl-3-methylpyrazine | Yes | Strong | Yes |
| 2-Isobutyl-3-methoxypyrazine | Yes | Strong | Yes |
| 2-Isopropylpyrazine | Yes | Strong | No |
| 2-Isobutylpyrazine | Yes | Strong | No |
| TS-72-1 | Yes | Strong | No |
| TS-72-2 | Yes | Strong | No |
| TS-73 (*) | No | — | No |
| 2-Acetylpyrazine (*) | No | — | Yes |

(*) Comparative Examples

TS-72-1: mixture of approx. 54 wt.-% methylpyrazine having one isopropyl substituent, approx. 38 wt.-% methylpyrazine having two isopropyl substituents and approx. 8 wt.-% methylpyrazine having three isopropyl substituents TS-72-2: mixture of approx. 11 wt.-% methylpyrazine having one isopropyl substituent, approx. 84 wt.-% methylpyrazine having two isopropyl substituents and approx. 5 wt.-% methylpyrazine having three isopropyl substituents TS-73: 100 wt.-% of methylpyrazine having three isopropyl substituents As it is evident from these results, the alkyl pyrazine compounds or mixtures thereof according to embodiments of the invention provide for a superior antimicrobial activity compared for instance with alkyl pyrazine compounds not having at least one isopropyl and/or isobutyl substituent.

Example 2

The alkyl pyrazine compounds according to embodiments of the invention have been tested for their efficacy against various microorganisms. The results are shown in Table 2.

TABLE 2

| Microorganism | Concentration (v/v) | Reduction | Time |
| --- | --- | --- | --- |
| *Escherichia coil* [1] | | | |
| *Stenotrophomonas maitophilia* [1] | | | |
| *Pseudomonas aeruginosa* [1] | | | |
| *Salmonella typhimurium* [1] | | | |
| *Bacillus subtilis* [2] | 0.1%-0.6% | 6-log | <5 min. |
| *Listeria monocytogenes* [2] | | | |
| *Nocardia* sp. [2] | | | |
| *Staphylococcus aureus* [2] | | | |
| *Staphylococcus epidermis* [2] | | | |

TABLE 2-continued

| Microorganism | Concentration (v/v) | Reduction | Time |
|---|---|---|---|
| Candida albicans [3] | 0.2%-0.8% | 4-log | <10 min. |
| Penicillium sp. [4] | 0.3%-0.9% | 3-log | <15 min. |

[1] gram-negative bacteria
[2] gram-positive bacteria
[3] yeast-like fungi
[4] mould-like fungi Example 3

The alkyl pyrazine compounds according to embodiments of the invention have been tested for their encapsulation in beta-cyclodextrin and controlled release. The results for a butylated alkyl pyrazine compound are shown in the FIGURE.

Abbreviations

CD: cyclodextrin
RT: room temperature
A280: absorbance at 280 nm

As shown in the FIGURE, the absorbance of the alkyl pyrazine is largely reduced in the presence of beta-cydodextrin1 which proves that the beta-cyclodextrin is capable of efficiently encapsulating the alkyl pyrazine. In addition, the experimental results shown in FIG. 1 reveal that the encapsulation by betacyclodextrin allows for a controlled release of the alkyl pyrazine compound.

While embodiments of the invention have been described in detail by way of specific embodiments and examples, the invention is not limited thereto and various alterations and modifications are possible, without departing from the scope of the invention.

The invention claimed is:

1. An antimicrobial composition comprising an alkyl pyrazine compound or mixture of compounds selected from the group consisting of 2-isobutyl-3-methylpyrazine, 2-isobutyl-3-methoxypyrazine, 2-isopropylpyrazine, 2-isobutylpyrazine and mixtures of methylpyrazines having one, two and three isopropyl or isobutyl substituents; and
    a carrier material comprising a cyclodextrin,
        wherein the alkyl pyrazine compound or mixture of compounds is immobilized on and/or in the carrier material.

2. The antimicrobial composition according to claim 1 further comprising an additional alkyl pyrazine compound having at least one isopropyl and/or isobutyl substituent.

3. The antimicrobial composition according to claim 1 being present in solid or liquid form.

4. The antimicrobial composition according to claim 1 further comprising a solvent.

* * * * *

UNITED STATES PATENT AND TRADEMARK OFFICE
CERTIFICATE OF CORRECTION

PATENT NO. : 10,881,107 B2
APPLICATION NO. : 15/752204
DATED : January 5, 2021
INVENTOR(S) : Stefan Liebminger, Gabriele Berg and Laura Lange It is certified that error appears in the above-identified patent and that said Letters Patent is hereby corrected as shown below:

On the Title Page

Item (56) OTHER PUBLICATION,    Delete "Schulz etal.",
    Insert --Schulz et al.--

In the Specification

Column 8, Line 64,    Delete "<5 min.",
    Insert --$\leq$ 5 min.--

Column 9, Line 6,    Delete "<10 min.",
    Insert --$\leq$10 min.--

Column 9, Line 7,    Delete "<15 min.",
    Insert --$\leq$15 min.--

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*